(12) United States Patent
Braun et al.

(10) Patent No.: US 6,555,377 B1
(45) Date of Patent: Apr. 29, 2003

(54) PROCESS FOR PRODUCTION OF MAMMALIAN CELL LINES

(75) Inventors: Serge Braun, Dorlisheim (FR); Frederic Perraud, Geudertheim (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/559,782

(22) Filed: Apr. 27, 2000

Related U.S. Application Data
(60) Provisional application No. 60/186,763, filed on Mar. 3, 2000.

(30) Foreign Application Priority Data

Apr. 27, 1999 (EP) .............................................. 99401032

(51) Int. Cl.⁷ ............................. C12N 15/85; C12N 5/02
(52) U.S. Cl. ........................................ 435/467; 435/377
(58) Field of Search ................................. 435/377, 467

(56) References Cited

U.S. PATENT DOCUMENTS

| | | |
|---|---|---|
| 4,699,880 A | 10/1987 | Goldstein |
| 4,711,955 A | 12/1987 | Ward et al. |
| 5,525,711 A | 6/1996 | Hawkins et al. |
| 5,529,920 A * | 6/1996 | Cole et al. ..................... 435/6 |
| 5,792,608 A | 8/1998 | Swaminathan et al. |

FOREIGN PATENT DOCUMENTS

| | | |
|---|---|---|
| WO | 0 302 175 | 2/1989 |

OTHER PUBLICATIONS

Fogel and Defendi, 1967, PNAS 58, 967–973.
Katakura et al, 1998, Methods Cell Biol., 57, 69–91.
Wolff et al, Science 247 (1990) 1465–1468.
Ledley, Human Gene Therapy 6 (1995) 1129–1144.
Geley et al, 1996, Review of Physiology, Biochemistry and Pharmacology, 128, 1–97.
Tresco et al, 1992, ASAIO J., 38, 17–23.
Aebischer et al, 1996, Hum. Gene Ther., 7, 851–860.
Deglon et al, 1996, Hum. Gene Ther., 7, 2135–2146.

* cited by examiner

*Primary Examiner*—Terry McKelvey
(74) *Attorney, Agent, or Firm*—Burns, Doane, Swecker & Mathis, L.L.P.

(57) ABSTRACT

Described is a process for generating a mammalian cell line from primary mammalian cells, comprising the step of:
- a) pre-treating a culture of said primary mammalian cells or a suspension thereof with at least one glucocorticoid,
- b) optional step comprising obtaining a suspension of said pre-treated culture of step a),
- c) transferring into the pre-treated cells of the suspension of step a) or b) at least one nucleic acid vector which is not of retroviral origin and which is competent to immortalize said pre-treated cells and
- d) culturing the transferred cells of step c).

Furthermore, mammalian cell lines and cells obtainable by the described process are provided as well as pharmaceutical and diagnostic compositions containing such cells.

21 Claims, 1 Drawing Sheet

LTR: RSV, LTR promoter.
Phleo: Phleomycin resistance gene.
MTII: Mouse metallothionein II gene promoter.
SV40 t+T: Large T and Small t SV40 antigens coding regions.

PROCESS FOR PRODUCTION OF MAMMALIAN CELL LINES

This application claims priority under 35 U.S.C. §§119 (e) to Provisional Application Ser. No. 60/186,763 filed in the United States on Mar. 3, 2000; the entire content of which is hereby incorporated by reference.

The present invention relates generally to the fields of process for generating mammalian cell lines, especially human cell lines, and preferably human muscular cell lines, to cell lines produced by this process and to uses of these cell lines, especially in gene therapy.

Cell lines are widely used as in vitro models for studying the events involved during in vivo cellular or tissular development. For example, muscular development events can be reproduced during the differentiation of muscle cell lines. Accordingly, permanent mammalian cell lines, especially human cell lines, would be of considerable value for providing useful tools for dissecting the molecular and biochemical cellular events, for identifying and testing new drugs for mammalian diseases, such as dystrophies, for the study of myogenesis, etc . . .

The ability to establish particular cell lines in culture that continue to express properties characteristic of the cells in the tissue from which they were derived would have obvious advantages for studying effects of drugs and potentially toxic substances or for developping cellular gene therapy. Many, but not all, cell types have been propagated in culture, and some maintain their original characteristics although many lose their differentiated phenotype upon continuous passage in culture. The two major properties of cell lines are their capability to proliferate and to differentiate.

Many studies have shown that the action of multiple oncogenes is sufficient to convert primary cells into immortalized transformed cells. For example, Fogel et Defendi, 1967, PNAS, 58, 967–973 demonstrated that human myoblasts were susceptibles to infection with wild-type SV40 and that permanent cell lines could be generated following infection, however these rapidly lost the ability to differenciate.

Accordingly, the prior art is deficient in providing a satisfactory means for establishing mammalian, and especially human immortal cell lines. The present invention fulfills this longstanding need and desire in the art.

The present invention provides an improved process for establishing long-term mammalian cell line, from primary cells isolated from tissues biopsie or primary cell culture, especially originating from muscular biopsies obtained from Duchenne muscular dystrophy patients as well as from normal, dystrophin-positive individuals. The cell lines obtained according to the present invention show an great proliferative capacity and may prove valuable for in vitro investigations related to the cellular and molecular metabolisms, to new drug screening or to methods assessing for cellular toxicity or cellular damages.

Thus, the present invention first concerns a process for generating a mammalian cell line from primary mammalian cells, comprising the step of:
  a) pre-treating a culture of said primary mammalian cells or a suspension thereof with at least one glucocorticoid,
  b) optional step comprising obtaining a suspension of said pre-treated culture of step a),
  c) transferring into the pre-treated cells of the suspension of step a) or b) at least one nucleic acid vector which is not of retroviral origin and which is competent to immortalize said pre-treated cells and
  d) culturing the transferred cells of step c).

Figure 1:
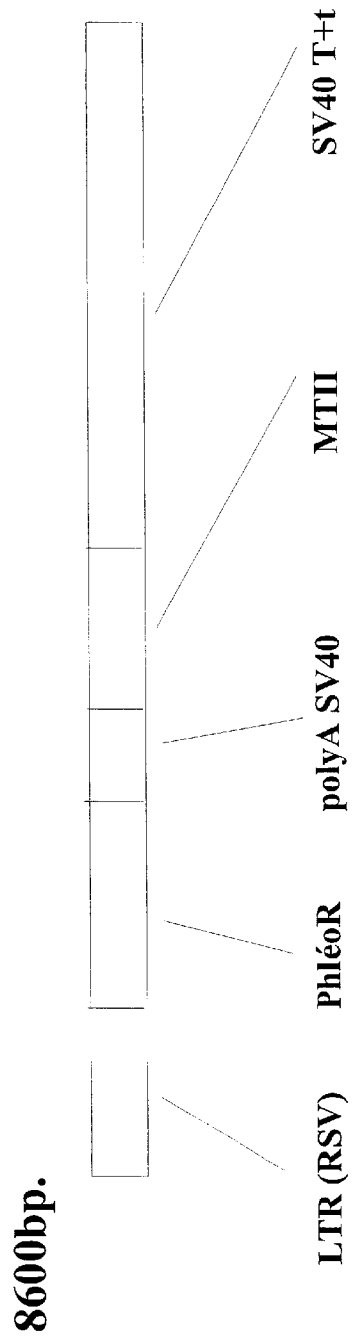
FIG. 1 shows the structure of pPhMT.

According to a first embodiment, the process of the present invention comprises the step of:
  a) obtaining a culture of said primary mammalian cells,
  b) pre-treating the culture of step a) with at least one glucocorticoid,
  c) obtaining a suspension of said pre-treated culture of step b),
  d) transferring into the pre-treated cells of the suspension of step c) at least one nucleic acid vector which is not of retroviral origin and which is competent to immortalize said pre-treated cells, and
  e) culturing the transferred cells of step d).

According to a second embodiment said process comprises the step of:
  a) obtaining a culture of said primary human muscular cells,
  b) obtaining a suspension of said cultured primary human muscular cells of step a),
  c) pre-treating the suspension of step b) with at least one glucocorticoid,
  d) transferring into the pre-treated cells of the suspension of step c) at least one nucleic acid vector which is not of retroviral origin and which is competent to immortalize said pre-treated cells and
  e) culturing the transferred cells of step d).

According to the present invention, the transferring step should preferably be performed on a cell suspension. Accordingly, in the special case where the cultured primary mammalian cells of step a) are not in the form of a suspension, the process should comprises a specific step consisting in obtaining a suspension of cultured primary mammalian cells or of pre-treated culture thereof.

According to a preferred embodiment, the cell suspension is extemporaneously prepared before the transferring step.

"Suspension of cells" means that the cells do not adhere to solid support.

Methods for preparing suspension of cells are disclosed in litterature and may comprises a treatment of primary mammalian cells culture or of tissue by mechanical tools (scraping, crushing; . . . ) or by chemical treatment with at least one compound capable of disaggregating cell organization, for example an enzyme selected from the group consisting of pancreatin, collagenase, dispase, trypsin, hyaluronidase, and equivalents thereof, with EDTA or by temperature variation (e.g., 4° C. treatment). Said compound or equivalent include all natural, modified or part of said compound or enzyme which is still capable of disaggregating cell organization and producing isolated cells which can easily be suspended. These mechanical or chemical treatments are widely used, have been reported in the literature (Tissue dissociation Guide, Worthington Biochemical Corporation) and can be readily obtained or adapted by those skilled in the art.

For example, cell organization may be dissociated by successive treatments with trypsin, for example 0.05% trypsin—EDTA 37° C. in a trypsinization flask with constant stirring. The cells collected in the supernatent after each trypsin treatment are pooled and cooled to 4° C. on ice. Calf serum is added to a final concentration of 10% (vol/vol) to terminate further protease activity. The dissociated cells are then centrifuged and the cell pellet is resuspended in conditioned media and either plated in culture, frozen in liquid nitrogen or submitted to the process of the instant invention.

According to a special embodiment, the primary mammalian cells of interest may be enriched to greater than 70%, preferably greater than 90% and more preferably greater than 99% purity by using a method of enrichment widely used in the art, such as cell purification using monoclonal antibodies or preplating methods based on adherence properties.

According to step a) of the process, a culture of primary mammalian cells is obtained. Cellular culture methods are widely used in the technical field of the present invention and the skilled man can easily select the media and growth conditions adapted to the initial primary mammalian cells sample used.

The invention is based on a specific step comprising a pre-treatment of the cultured primary mammalian cells, eventually in the form of a suspension, with at least one glucocorticoid. Generally, any glucocorticoid may be used in the process of the present invention. Representative examples of useful glucocorticoids include dexamethasone, betamethasone, budesonide, hydrocortisone, prednisone, prednisolone, triamcinolone and flunisolide. The glucocorticoid may be either in a lipid soluble form, an ethanol soluble form or a water soluble form, and may further be either a synthetic or a non-synthetic glucocorticoid.

The pre-treatment step consists more particularly in contacting said cultured primary mammalian cells or a suspension thereof with at least one glucocorticoid. This pre-treatment of primary mammalian cells may be applied at least 3 hours, preferably at least 24 hours, and more preferably at least 48 hours before the transferring step.

The glucocorticoid concentration in the cells pre-treatment step ranges from $10^{-4}$ M to $10^{-10}$ M. In the specific case where the glucocorticoid is dexamethasone or hydrocortisone, said glucocorticoid concentration should preferably be ranging near $10^{-6}$ M or $10^{-5}$ M, respectively.

Although the process of the invention should at least comprise a glucocorticoid pre-treatment of the cells before the transferring step, according to a specific embodiment, it is also possible to envisage the use of said glucocorticoid in the steps consisting in obtaining a cell suspension or in transferring the nucleic acid vector.

Another essential step of the process leading to generate mammalian cell line of the invention, consists in introducing into pre-treated cells a nucleic acid vector competent to immortalize said pre-treated cells.

"Nucleic acid sequence competent to immortalize cells" means that due to the expression of a nucleic acid sequence competent to immortalize cells, cells were capable of in vitro growth for at least 100 doublings, compared with the normal situation where senescence occurs after 30 doublings, they are considered to be immortal. Transforming oncogenes are for example those which produce foci of transformed cells in a monolayer of NIH3T3 cells.

Literature provides many examples of such nucleic acid sequences which are competent to immortalize cells (Katakura et al., 1998, Methods Cell Biol., 57, 69–91). According to a preferred embodiment, this nucleic acid vector comprises at least one nucleic acid sequence encoding an oncogenic polypeptide selected from the group consisting of myc, SV40 T antigen, SV40 t antigen, papillomaviruses E6 and E7, polyoma Large T gene, EBV, ras, adenovirus E1, p53 and oncogenic parts thereof.

In order to permit introduction and expression of said immortalizing nucleic acid sequence into targeted cell, it is incorporated into a nucleic acid vector comprising genetic elements necessary for the expression of said nucleic acid sequence into said cell.

According to the present invention, "nucleic acid vector" means a nucleic acid construct which may be either a DNA and/or RNA, single or double-stranded, linear or circular, natural or synthetic, modified or not (see U.S. Pat. Nos. 5,525,711; 4,711,955; 5,792,608 or EP-A-302,175 for modification examples) defining a fragment or a portion of a nucleic acid, without size limitation. It may be, inter alia, a genomic DNA, a cDNA, a mRNA, an antisense RNA, a ribozyme, or DNA encoding such RNAs. The "nucleic acid vector" may be in the form of linear nucleic acid construct, and preferably in the form of plasmid. According to the invention, said "nucleic acid vector" should preferably be understood as a naked nucleic acid construct (Wolff et al., Science 247 (1990), 1465–1468) or as nucleic acid construct formulated with at least one compound such as polypeptides, preferably viral polypeptides, or cationic lipids or cationic polymers which can participate in the uptake of the nucleic acid construct into the cells (see Ledley, Human Gene Therapy 6 (1995), 1129–1144 for a review). According to the present invention, the "nucleic acid vector" should contain at least one nucleic acid sequence competent to immortalize cells pre-treated according to the process of the invention. As this particular sequence encodes at least one polypeptide which is involved in cellular immortalization, said "nucleic acid vector" should further contain elements necessary for expression of said nucleic acid sequence. Transcriptional promoters suitable for use in various vertebrate systems are well known. For example, suitable promoters include viral promoters like RSV, MPSV, SV40, CMV or 7.5k, vaccinia promoter, inducible promoters, metalothionein promoter, etc. According to a particular preferred embodiment, said elements necessary for the expression of the nucleic acid sequence are activable by glucocorticoid (Geley et al., 1996, Review of Physiology, Biochemistry and Pharmacology, 128, 1–97). The "nucleic acid vector" can further include intron sequences, targeting sequences, transport sequences, sequences involved in replication or integration or selective sequence encoding for example antibiotic resistance (ampicilin, phleomycin, chloramphenicol, . . . ). Example of such sequences have been reported in the literature and can be readily obtained by those skilled in the art. The "nucleic acid vector" can also be modified in order to be stabilized with specific components such as spermine.

In a further preferred embodiment, the nucleic acid vector further comprises at least one second nucleic acid sequence encoding all or part of a therapeutic or prophylactic polypeptide. Examples of such polypeptides are enzymes, hormones, cytokines, membrane receptors, targetting polypeptide, structural polypeptides, transport polypeptides, tumoral, viral or infectious antigens, adhesines, albumin, ligands, transcription factors, traduction factors, replication factors, stabilization factors, antibodies, E6 or E7 from HPV, MUC1, BRCA1, interferons, interleukin (IL-2, IL-4, IL-6, IL-7, IL-12), GM-CSF (Granulocyte Macrophage Colony Stimulating Factor), the tk gene from Herpes Simplex type 1 virus (HSV-1) or VEGF. According to a preferred embodiment, said nucleic acid sequence encodes all or part of dystrophin. Furthermore, said DNA may encode all or part of a polypeptide which is an immunity conferring polypeptide and acts as endogenous immunogen to provoke a humoral or cellular response, or both, against infectious agents, including intracellular viruses, and also against tumor cells. An "immunity conferring polypeptide" means that said polypeptide when it is expressed can participate to an immune response into a treated patient. The polynucleotide can also code for an antibody. In this regard, antibody encompasses whole immunoglobin of any class, chimeric antibodies and hybrid antibodies with dual or multiple antigen or epitope specificities, and fragments, such as F(ab)'$_2$, Fab', Fab including hybrid fragments and anti-idiotypes (U.S. Pat. No. 4,699,880).

According to the transferring step, the nucleic acid sequence, or more broadly the nucleic acid vector comprising said sequence, is transferred into a pre-treated cell in suspension by any of a wide variety of ways, including a method selected from the group consisting of adenoviral infection, transfection with nucleic acid coated particles such as lipoplexes (cationic lipid/nucleic acid complexes) or polyplexes (cationic polymer/nucleic acid complexes) or the like, calcium phosphate transfection of plasmid, transfection with naked nucleic acid, electroporation method and/or any combination thereof. However, the particular method for introducing the foreign nucleic acid sequence is not crucial to the invention.

In a particular embodiment, the transferring step of the process is performed in presence of at least one glucocorticoid. The glucocorticoid used in said transferring step can be identical or different from the one used in cellular pre-treatment step.

Usually, the nucleic acid concentration in the transferring step will be selected to range from 0.1 to 100 $\mu g/10^6$ cells.

The primary mammalian cell treated according to the process described above includes those of various tissular origin, and preferably is selected from the group consisting of lymphocyte, fibroblast, vein endothelium, retinal cells, endothelial cells, Schwann cells and osteoblast. In another preferred embodiment, the process of the present invention is implemented with muscular primary cells selected from the group consisting of skeletal muscle cells, smooth muscle cells, and preferably myoblasts or myotubes. More specifically, said primary mammalian cell is a myoblast or a satellite cell. According to a preferred embodiment, the primary mammalian cell suspension which is cultured in step a) comprises at least muscular cells, and preferably myocytes, nevertheless, a mammalian cell line can also be obtained by treating primary cell suspension incorporating non-muscular cells (i.e. fibroblasts, etc . . . ). In this special case, further selection can easily permit mammalian cell line selection. Preferably said primary mammalian cell is of human origin.

The invention concerns more particularly a mammalian cell line generated as previously described by a specific treatment of primary mammalian cells. According to a specific embodiment, said mammalian cell line is not a muscular cell line.

The present invention further concerns a mammalian cell line as previously described which is further modified by introducing a second nucleic acid sequence encoding all or part of a therapeutic or prophylactic polypeptide. Said second nucleic acid sequence is as previously defined and preferably encodes all or part of dystrophin or of a immunity-conferring polypeptide.

The invention also provides mammalian cells isolated from a mammalian cell line of the present invention.

The present invention further concerns a pharmaceutical composition comprising at least one mammalian cell isolated from a mammalian cell line of the present invention, and preferably a cell which is not of muscular origin. According to a preferred embodiment, said mammalian cell comprised in said pharmaceutical composition is encapsulated. Cell encapsulation methodology has been previously described which allows transplantation of encapsulated cells in treatment of Parkinson's disease (Tresco et al., 1992, ASAIO J., 38, 17–23) or Amyotrophic lateral sclerosis (Aebischer et al., 1996, Hum. Gene Ther., 7, 851–860). According to said specific embodiment, cells are encapsulated by compounds which form a microporous membrane, and said encapsulated cells can further be implanted in viva. Capsules, for example approximately 1 cm in length containing the cells of interest may be prepared employing a hollow microporous membrane fabricated from poly-ether-sulfone (PES) (Akzo Nobel Faser AG, Wuppertal, Germany; Deglon et al, 1996, Hum. Gene Ther., 7, 2135–2146). This membrane has a molecular weight cutoff greater than 1,000,000 Da, which permits the free passage of proteins and nutrients between the capsule interior and exterior, while preventing the contact of transplanted cells with host cells. The entrapped cells may be implanted by intradermal, subdermal, intravenous, intramuscular, intranasal, intracerebral, intratracheal, intraarterial, intraperitoneal, intravesical, intrapleural, intracoronary or intratumoral ways.

In a further embodiment, the invention relates to the use of at least one mammalian cell generated, and eventually modified, as described above for the preparation of a composition for administration into a human tissue. In a preferred embodiment the prepared composition in accordance with the use claimed in the present invention is in a form for administration into a vertebrate tissue. These tissues include those of muscle, skin, nose, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, tumor etc. The administration may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Moreover, myoblast cells are found to migrate from the original site of-administration to other sites, particularly injured sites, e.g. degenerating foci. This migration phenomenom permits the treatment of injured sites by injecting myoblasts into the patient in need, particularly in tissue, usually muscle tissue, proximal to the injuries, although injection into the circulation or at a distal site may also be possible. By employing genetically engineered myoblasts one may provide for directed application of products of interest to the injured region. Usually, cell injection will be about $10^4$ to $10^7$ cells (modified or not) per $cm^3$ of muscle tissue to be treated. In this particular case, the composition according to the invention may also comprise a pharmaceutically acceptable injectable carrier. The carrier is preferably isotonic, hypotonic or weakly hypertonic and has a relatively low ionic strength, such as provided by a sucrose solution. It includes any relevant solvent, aqueous or partly aqueous liquid carrier comprising sterile, pyrogen-free water, dispersion media, coatings, and/or equivalents. The pH of the pharmaceutical preparation is suitably adjusted and buffered.

From yet another perspective, the invention relates to a diagnostic kit comprising at least one mammalian cell generated according to the invention for in vitro assessment of muscular cellular toxicity or damages of candidate or commercially available pharmaceutical molecules (pre-clinical assays) or for in vitro screening of new drugs. The cell lines may also serve as a tool to analyse physiopathology of cellular diseases.

While the present invention has been described with reference to preferred embodiments and specific examples, one of the ordinary skill after reading the foregoing specification will be able to effect various changes, substitutions of equivalents, and other alterations to the processes and produced cells set forth herein. It is therefore intended that the protection claimed hereon be limited only by the definition contained in the appended claims and equivalents thereof.

EXAMPLES

Establishment of Human Cell Lines from (i) a Healthy Donor and (ii) a Patient with Duchenne Muscular Dystrophy by the Process of the Present Invention 1. Materials The plasmid DNA (pPHMT—FIG. 1) used in the transferring step contains T and t antigenes coding regions from SV40 placed under the control of the mouse metallothionein II promoter. Selection gene is the procaryotic phleomycin resistance gene controlled by the LTR promoter from RSV.

2. Process of the Invention a) Culture of primary human muscular cells.

Myoblasts were obtained from muscles biopsies of a metabolically healthy patient after orthopedic surgery or from a DMD patient. Cells are harvested from explant cultures and grown in Ham's F14 medium (Life Technologies) supplemented with 10% fetal calf serum (Hyclone, Logan, Utah), 10 g/ml insulin, 10 ng/ml epidermal growth factor (both from Sigma), 10 ng/ml basic fibroblast growth factor (Pepro Tech, Rocky Hill, N.J.), 2 mM glutamine (bioMerieux, Marcy l'Etoile, France) and 40 g/ml gentamycin (Schering Plough, Kenilworth, N.J.). The process is performed on myoblasts obtained after a maximum of 12 passages and seeded (3000 cells/cm5) on 0.1% gelatin-coated dishes (100 mm diameter). Muscle cells are characterized by immunocytochemistry for desmin, dystrophin (NCL anti-human dystrophin monoclonal antibodies, Novocastra) and their ability to fuse and to form myotubes. Proportion of myoblasts in the culture used for the next step of the process is between 70 and 90%.

b) Pre-treatement of the culture with dexamethasone.

Two days before transfection step, $5.10E5$ cells are seeded in 100 mm diameter culture dishes in culture medium supplemented with $10^{-6}$ M dexamethasone (Sigma) diluted in ethanol.

c) Preparation of a suspension of the pre-treated culture.

The pre-treated cell culture is submitted to a trypsination step using a 0.25% trypsin preparation. The culture medium is removed and the monolayer cells are rapidly rinced with few ml of trypsin preparation (Gibco). 0.5 ml of pre-warmed (37° C.) trypsin preparation is added. Trypsinisation step is performed for about 5 minutes at 37° C. and is monitored by inverted microscope observation of the monolayer cells. The cells from all dishes are collected by centrifugation and resuspended in 20 ml of dexamethasone containing culture medium, mecanically disrupted to complete the trypsinisation step and distributed in two sterile tubes.

d) Calcium phosphate transfection step.

1 ml of calcium phosphate precipitate (20 μg DNA/ml) is added in each tube and a 100 mm culture dish is seeded with 11 ml of the transfection mixture (cells+ precipitated plasmid DNA) for about 24 hours at 37° C., 5% CO2.

The transfected cells are then cultured in culture medium according to conventional culture method. The transfected clones are selected by adding phleomycin at 50 g/ml after 24 h. Dexamethasone is also added at each changement of culture medium until clones selection. The clone selection is performed by immunofluorescence staining.

According to this selection method, the transfected cells are cultured in Lab-Tek chamber slides (Nunc, Naperville, Ill., USA) for 2 days and fixed with methanol-acetone (1:1) for 10 min at −20 C. Slides are then incubated with anti-SV40 T antigen mouse monoclonal antibody (PAB-419; Chemicone) for 1 hour at room temperature, rinced with PBS buffer and rabbit anti-mouse IgG FITC-conjugated antibodies (ICN ImmunoBiologicals, Lisle, Ill., USA) is subsequently applied for 1 h at room temperature. Slides are mounted with a solution of Mowiol and examined under an epifluorescence microscope (Nikon).

3. Results

For human myoblasts a major problem is the refractoriness of those cells (healthy as well as DMD) to transfection. The transfection efficacy is very low when classical transfection techniques are used (around $10^{-7}$). It could now be demonstrated in accordance with the present invention that the combination of a glucocorticoid pre-treatment of the target cells together a with transfection step made on suspended cells allows the generation of immortalized clones (efficiency $10^{-5}$). For human DMD myoblasts, more than 15 clones were obtained, 3 of which were selected with regard to their ability to form myotubes. Moreover, it was observed that in order to preserve a good proliferating rate, the clones should preferably be plated at about 30% confluency. The isolated clones are preferably cultured in DMEM basal medium, 20%SVF, Insulin, EGF, bFGF, Dexamethasone and Zinc Sulfate.

Immunofluorescence study of clones demonstrated expression of SV40 TAg in all cells. The myoblasts natural marker "desmin" was also present, and some of the clones were able to fuse.

| Species | Number of clones obtained | Number of clones expressing TAg | Number of clones expressing Desmin | Number of fusing clones |
|---|---|---|---|---|
| Mdx | 19 | 19 | 3 | 0 |
| DMD | 33 | 33 | 10 | 3 |
| Healthy human | 21 | 20 | 5 | 4 |

Transfectability of the isolated cell lines has also been tested by calcium phosphate transfection using a plasmid expressing the Beta-Galactosidase gene (Beta-Gal).

Two of the identified clones were efficiently transfected: the clone MyohTG1 (healthy) (CNCM No I-2128) and MyohTGD24 (Duchenne) (CNCM No I-2127) which shown 1 to 10% of Beta-Gal expressing cells after transient transfection.

These two clones are able to proliferate, to differentiate and to express properties characteristic of muscular cells and further can efficiently transfected with nucleic acid vector usefull for expressing gene of interest into said cells.

The clones Myoh TG1 and Myoh TGD24 have been deposited on Feb. 16, 1999 with the Collection Nationale de Cultures de Microorganimes (CNCM), Institut Pasteur, 25, Rue du Docteur Roux, F-75724 Paris Cedex 15 and have been attributed the CNCM accession no. I-2128 and I-2127, respectively.

We claim:

1. A process for generating a mammalian cell line from primary mammalian cells, comprising:

a) pre-treating a culture of primary mammalian cells or a suspension thereof with at least one glucocorticoid, b) if said culture of primary mammalian cells is not in the form of a suspension, obtaining a suspension of the pre-treated culture of step a), c) transferring into the pre-treated cells of the suspension at least one nucleic acid vector which is not of retroviral origin and which is competent to immortalize said pre-treated cells, and d) culturing the transferred cells of step c).

2. A process for generating a mammalian cell line from primary mammalian cells, comprising:

a) obtaining a culture of said primary mammalian cells, b) pre-treating the culture of step a) with at least one glucocorticoid, c) obtaining a suspension of said pre-treated culture of step b), d) transferring into the pre-treated cells of the suspension of step c) at least one nucleic acid vector which is not of retroviral origin and which is competent to immortalize said pre-treated cells and e) culturing the transferred cells of step d).

3. A process for generating a mammalian cell line from primary human muscle cells, comprising:

a) obtaining a culture of said primary human muscle cells, b) obtaining a suspension of said cultured primary human muscle cells of step a), c) pre-treating the suspension of step b) with at least one glucocorticoid, d) transferring into the pre-treated cells of the suspension of step c) at least one nucleic acid vector which is not of retroviral origin and which is competent to immortalize said pre-treated cells and e) culturing the transferred cells of step d).

4. The process of claim 1, wherein said suspension is obtained by a treatment of said cultured primary mammalian cells or of said pre-treated culture with at least one compound capable of disaggregating cell organization.

5. The process of claim 4 wherein said compound is an enzyme selected from the group consisting of pancreatin, collagenase, dispase, trypsin, hyaluronidase, and equivalents of any one thereof.

6. The process of claim 1, wherein said glucocorticoid is dexamethasone, betamethasone, budesonide, hydrocortisone, prednisone, prednisolone, triamcinolone or flunisolide.

7. The process of claim 1, wherein said glucocorticoid is in a lipid soluble form, an ethanol soluble form or a water soluble form.

8. The process of claim 1, wherein said glucocorticoid is a synthetic glucocorticoid.

9. The process of claim 1, wherein said pre-treatment comprises contacting said culture of primary mammalian cells or a suspension thereof with said glucocorticoid.

10. The process of claim 9 wherein said pre-treatment is applied at least 3 hours before the transferring step.

11. The process of claim 9 wherein the glucocorticoid concentration in the pretreatment step ranges from $10^{-4}$ M to $10^{-10}$ M.

12. The process of claim 1, wherein said nucleic acid vector competent to immortalize cells comprises at least one nucleic acid sequence encoding an oncogenic polypeptide selected from the group consisting of myc, SV40 T antigen, SV40 t antigen, papillomaviruses E6 and E7, polyoma Large T gene, EBV, ras, adenovirus E1, p53 and oncogenic parts of any one thereof.

13. The process of claim 12 wherein said nucleic acid vector further comprises elements necessary for the expression of said nucleic acid sequence.

14. The process of claim 13, wherein said elements necessary for the expression of said nucleic acid sequence are activable by glucocorticoids.

15. The process of claim 13, wherein said nucleic acid vector is a plasmid.

16. The process of claim 13, wherein said nucleic acid vector further comprises a second nucleic acid sequence encoding all or part of a therapeutic or prophylactic polypeptide.

17. The process of claim 1, wherein the nucleic acid sequence competent to immortalize cells is transferred into pre-treated cells of said suspension by a method selected from the group consisting of viral infection, cationic lipid or cationic polymer transfection, calcium phosphate transfection, electroporation, and combinations of any one thereof.

18. The process of claim 1, wherein said transferring step is performed in presence of at least one glucocorticoid.

19. The process of claim 1, wherein the nucleic acid concentration in the transferring step ranges from 0.1 to 100 $\mu g/10^6$ cells.

20. The process of claim 1, wherein said primary mammalian cells are lymphocytes, fibroblasts, vein endothelium cells, retinal cells, endothelial cells, Schwann cells or osteoblasts.

21. The process of claim 1, wherein said glucocorticoid is a non-synthetic glucocorticoid.

* * * * *